United States Patent
Katada et al.

(10) Patent No.: US 7,123,680 B2
(45) Date of Patent: Oct. 17, 2006

(54) X-RAY COMPUTER TOMOGRAPHY APPARATUS

(75) Inventors: Kazuhiro Katada, Aichi-gun (JP); Toshihiro Rifu, Saitama (JP)

(73) Assignee: Toshiba Medical Systems Corporation, Otawara (JP)

( * ) Notice: Subject to any disclaimer, the term of this patent is extended or adjusted under 35 U.S.C. 154(b) by 8 days.

(21) Appl. No.: 10/941,810

(22) Filed: Sep. 16, 2004

(65) Prior Publication Data

US 2006/0008048 A1 Jan. 12, 2006

(30) Foreign Application Priority Data

Jul. 6, 2004 (JP) ............... 2004-198871

(51) Int. Cl.
*G21K 1/04* (2006.01)
(52) U.S. Cl. ......................... 378/16; 378/160
(58) Field of Classification Search .................. 378/15, 378/1, 2, 160, 16
See application file for complete search history.

(56) References Cited

U.S. PATENT DOCUMENTS

| | | | | |
|---|---|---|---|---|
| 4,195,229 A | * | 3/1980 | Suzuki | 378/16 |
| 4,241,404 A | * | 12/1980 | Lux | 378/2 |
| 4,534,051 A | * | 8/1985 | Grady et al. | 378/98.3 |
| 6,298,111 B1 | * | 10/2001 | Ozaki | 378/8 |
| 6,901,129 B1 | * | 5/2005 | Tachizaki et al. | 378/4 |

FOREIGN PATENT DOCUMENTS

| | | |
|---|---|---|
| JP | 52-63091 | 5/1977 |
| JP | 56-76200 | 6/1981 |

* cited by examiner

*Primary Examiner*—Edward J. Glick
*Assistant Examiner*—John M. Corbett
(74) *Attorney, Agent, or Firm*—Oblon, Spivak, McClelland, Maier & Neustadt, P.C.

(57) ABSTRACT

An X-ray computer tomography apparatus includes an X-ray tube, an X-ray detector, a data collection apparatus that collects X-ray signals from the X-ray detector repeatedly, a shutter mechanism that is arranged between the X-ray tube and a subject in order to convert an X-ray into a pulse-like X-ray and is constituted such that a ratio of a shutter open period and a shutter close period is variable, a restructuring unit that restructures image data on the basis of the collected X-ray signals, and a control unit that controls the shutter mechanism in order to change the ratio of a shutter open period and a shutter close period during a helical scan.

13 Claims, 7 Drawing Sheets

ROTATING DIRECTION

SHIFT DIRECTION

LOCUS OF CENTER OF X-RAY IRRADIATION RANGE DRAWN ON SHUTTER DISK 25

RANGE OF IRRADIATION OF X-RAY, WHICH IS FORMED BY COLLIMATOR 11, ON SHUTTER DISK 25 (POSITION FIXED)

SHIFT

RANGE OF IRRADIATION OF X-RAY ON SHUTTER DISK 25

X-RAY COMPUTER TOMOGRAPHY APPARATUS

CROSS-REFERENCES TO RELATED APPLICATIONS

This application is based upon and claims the benefit of priority from the prior Japanese Patent Application No. 2004-198871, filed Jul. 6, 2004, the entire contents of which are incorporated herein by reference.

BACKGROUND OF THE INVENTION

1. Field of the Invention

The present invention relates to an X-ray computer tomography apparatus.

2. Description of the Related Art

In a present X-ray computer tomography apparatus, continuous X-rays are mainly used. While X-rays are continuously irradiated on a subject, data collection is repeated at a constant cycle. A data collection cycle roughly consists of a charge storage period, a signal charge read-out period, and a charge reset period. Theoretically, only X-rays irradiated within the charge storage period are reflected on data. Therefore, it is effective for a reduction in exposure to irradiate a pulse-like X-ray on a subject in synchronization with the charge storage period rather than continuously irradiating X-rays on the subject. However, under the present situation in which an ultra-fast scan with a scan time of 0.5 seconds or less is mainly used, the irradiation of a pulse-like X-ray is not adopted because a load on a high-voltage generation apparatus is large. In addition, there is a disadvantage that, when it is attempted to create an X-ray of a short pulse, a surface exposure dose increases because an X-ray with low energy is generated at a rising edge of the pulse.

Therefore, as described in Japanese Patent Nos. 2704084, 2768932, and 3394038 and JP-A-10-295681, under the present situation, an exposure dose is adjusted according to tube current control.

BRIEF SUMMARY OF THE INVENTION

It is an object of the invention to realize adjustment for an exposure dose according to pulse width control for an X-ray.

An X-ray computer tomography apparatus according to the invention includes: an X-ray tube that generates an X-ray; an X-ray detector for detecting an X-ray transmitted through a subject; a collection unit that collects X-ray signals from the X-ray detector repeatedly; a shutter mechanism unit that is arranged between the X-ray tube and the subject in order to convert the generated X-ray into a pulse X-ray and is constituted such that a ratio of a shutter open period and a shutter close period is variable; a restructuring unit that restructures image data on the basis of the collected X-ray signals; and a control unit that controls the shutter mechanism unit in order to change the ratio of a shutter open period and a shutter close period.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Embodiments of an X-ray computer tomography apparatus according to the invention will be hereinafter explained with reference to the accompanying drawings. Note that, as a system for the X-ray computer tomography apparatus, there are various systems such as a rotating/rotating system in which an X-ray tube and an X-ray detector rotate around a subject as one body, a fixed/rotating system in which plural X-ray detectors are arranged on a ring and only an X-ray tube rotates around a subject, and a fixed/fixed system in which plural X-ray tubes are arranged on a ring and plural X-ray detectors are also arranged on the ring. The invention is applicable to all of these systems. As a type of the rotating/rotating system, there are a one-tube type in which a pair of X-ray tube and X-ray detector are mounted on a rotary frame and a so-called multi-tube type in which plural pairs of X-ray tube and X-ray detector are mounted on a rotary frame. The invention is applicable to both the types. As a type of the X-ray detector, there are an indirect conversion type that converts an X-ray transmitted through a subject into light with a phosphor such as a scintillator and then converts the light into a charge with a photoelectric conversion element such as a photodiode and a direct conversion type that utilizes generation of an electron hole pair in a semiconductor by an X-ray and movement of the electron hole pair to an electrode, that is, a photoconduction phenomenon. The invention may adopt both the types.

Figure 1:
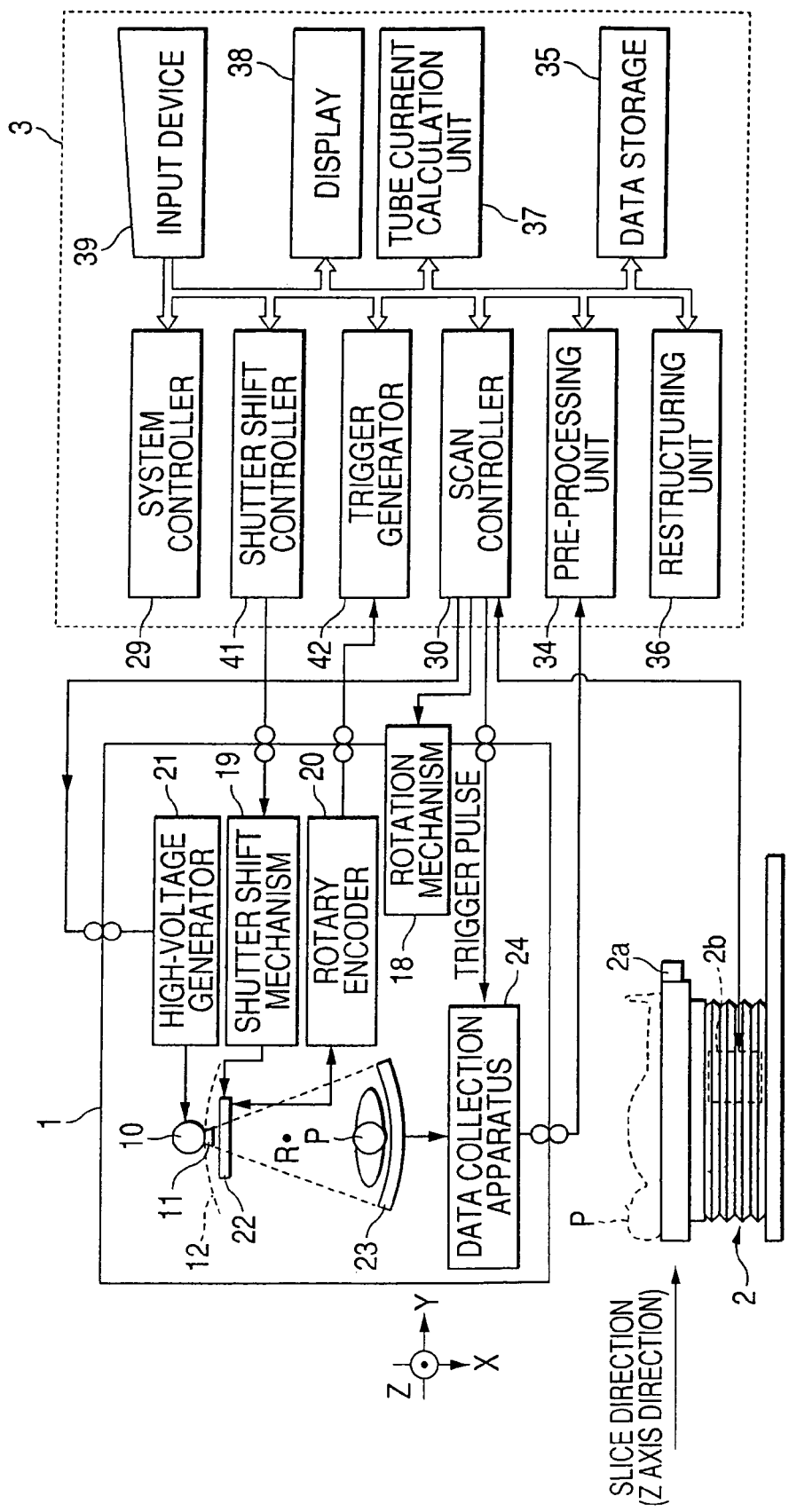
FIG. 1 is a diagram showing a structure of an X-ray computer tomography apparatus in accordance with an embodiment of the invention.

FIG. 1 shows a structure of an X-ray computer tomography apparatus in accordance with this embodiment. A gantry 1 houses a rotary frame 12 of a substantially annular shape. A rotary mechanism 18 supports the rotary frame 12 so as to be rotatable around a rotation axis R and includes a drive system therefor. An X-ray tube 10 and a multi-channel type X-ray detector 23 having plural X-ray detection elements, which are arranged in an arc shape around an X-ray focus of the X-ray tube 10, are attached to the rotary frame 12 so as to be opposed to each other across a subject placed on a top plate 2a of a bed 2. A high-voltage generator 21 is provided in order to apply a high voltage to a part between a cathode and an anode of the X-ray tube 10 and supply a filament heating current to a cathode filament.

The X-ray tube 10 is housed in a housing of heavy metal with a high X-ray shielding property. A part of the housing is opened, and an X-ray radiation window made of a material with high radiolucency is fit into the opened part. A collimator 11 is attached to a part of the housing corresponding to the X-ray radiation window. An X-ray radiated from the X-ray radiation window is formed in a predetermined shape by the collimator 11. Note that, for convenience of explanation, a rotation center axis of the rotary frame 12 is defined as a Z axis to define a rotating coordinate system with orthogonal three axes that rotates around the Z axis in accordance with the rotation of the rotary frame 12. An X axis is defined on a line that connects a center of a spot (X-ray focus) on an anode target in the X-ray tube 10, against which an electron beam generated in the cathode collides, and a center of an element arrangement of the X-ray detector 23, that is, a center line of an X-ray beam of a conical or pyramid shape radiated from the collimator 11.

A shutter mechanism 22 is arranged between the collimator 11 and a subject and is actually attached to an exit port of the collimator 11. The shutter mechanism 22 has a function of converting X-rays continuously generated by the X-ray tube 10 into a pulse X-ray that is repeated at a constant cycle. In addition, the shutter mechanism 22 has a function of changing a pulse width (also called a pulse duration) while keeping the period of the pulse X-ray constant. A structure of the shutter mechanism 22 will be hereinafter explained in detail.

Figure 2:
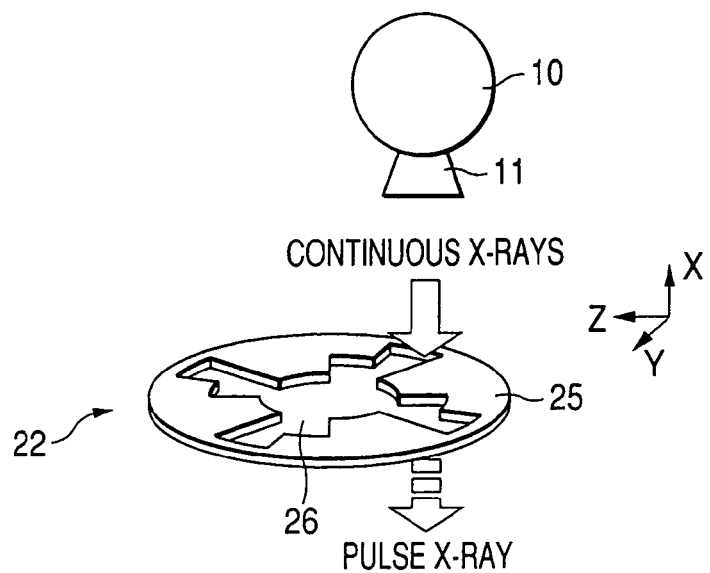
FIG. 2 is a diagram showing an arrangement of a shutter mechanism in FIG. 1.

As shown in FIG. 2, the shutter mechanism 22 includes a disc-like shutter disk 25 that is obtained by reinforcing a plate of heavy metal represented by lead having a high X-ray shielding property with a plate of iron or the like having high rigidity. The shutter disk 25 is arranged such that a surface thereof is substantially perpendicular to a center axis of an X-ray. Although not shown in the figure, the shutter mechanism 22 has a shutter disk rotation mechanism together with the shutter disk 25. The shutter disk rotation mechanism includes a drive system, which drives the shutter disk 25 to rotate at a constant speed, together with a structure for rotatably supporting the shutter disk 25 with a disc center line thereof as a rotation axis. The rotation axis of the shutter disk 25 is provided substantially parallel with the X axis. A rotation speed of the shutter disk 25 is set to a speed corresponding to a data collection cycle of a data collection apparatus 24.

Figure 3:
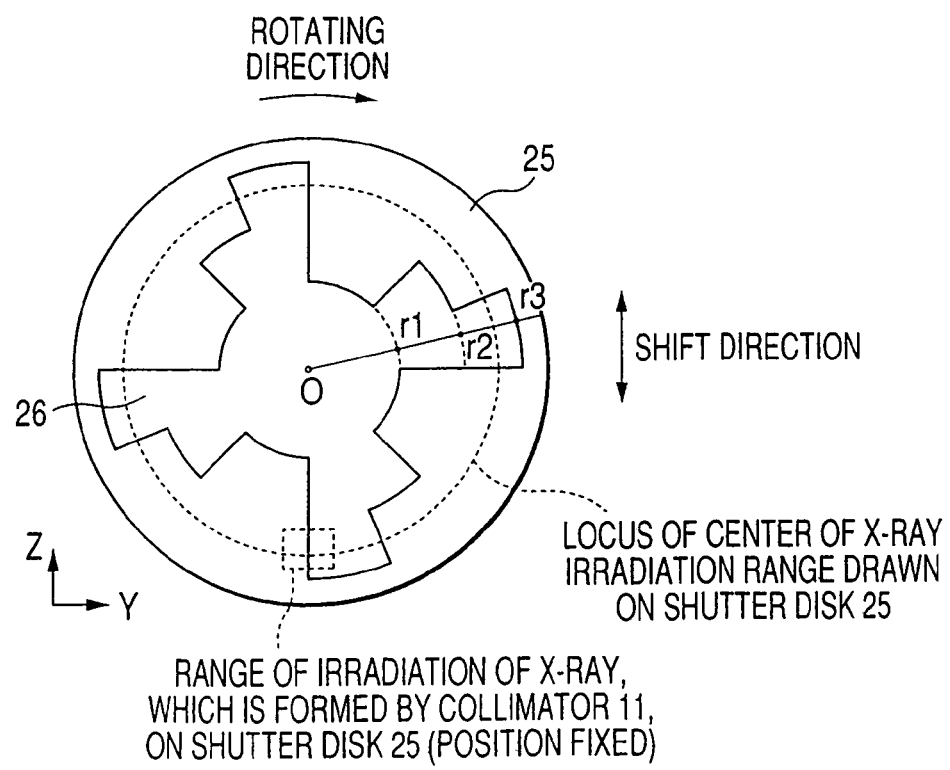
FIG. 3 is a plan view of a shutter disk in FIG. 2.

At least one aperture 26 is opened in the shutter disk 25. The aperture 26 has a shape in which an aperture ratio in a circumferential direction changes with respect to a radial direction. The aperture ratio represents a ratio of a length in the circumferential direction of one aperture 26 with respect to 1/n of a length of a circumference where the number of apertures 26 is n. If the aperture 26 is long in the circumferential direction, the aperture ratio is high. On the contrary, if the aperture 26 is short in the circumferential direction, the aperture ratio is low. In accordance with the change in the aperture ratio, a ratio of a shutter open period and a shutter close period changes. A specific example of the shape of the aperture 26 is shown in FIG. 3. In this example, four apertures 26 are formed at a constant interval (90°) in the circumferential direction. The number of apertures 26 is not required to be limited to four.

Each of the apertures 26 has an aperture width with an aperture ratio of 1.0 in a range from a center O of the disk 25 to a radius r1. In other words, the four apertures 26 are united in this range. Each of the apertures 26 has an aperture width with an aperture ratio of 0.7 in a range from the radius r1 to a radius r2 and has an aperture width with an aperture ratio of 0.3 in a range from the radius r2 to a radius r3. In this way, the apertures 26 are formed such that the aperture ratio changes stepwise with respect to the radial direction of the disk 25. Although the number of steps is "3" in this example, the number may be two or may be set to an arbitrary number of four or more without limitation.

With such a structure, when an irradiation position of an X-ray on the disk 25 is adjusted to be within the range from the center O of the disk 25 to the radius r1, a shutter effect with respect to the X-ray is not shown, and as in the conventional technique, the X-ray is irradiated on a subject over an entire period of the data collection cycle consisting of the charge storage period, the signal charge read-out period, and the charge reset period. When an irradiation position of an X-ray on the disk 25 is adjusted to be within the range from the radius r1 to the radius r2, the X-ray is irradiated on a subject only in a period of 70% of the data collection cycle. When an irradiation position of an X-ray on the disk 25 is adjusted to be within the range from the radius r2 to the radius r3, the X-ray is irradiated on a subject only in a period of 30% of the data collection cycle. In other words, the apertures 26 are formed in the disk 25 having the shape shown in FIG. 3 such that the shutter effect increases stepwise from the center of the disk 25 toward an outer circumference thereof.

Figure 4:
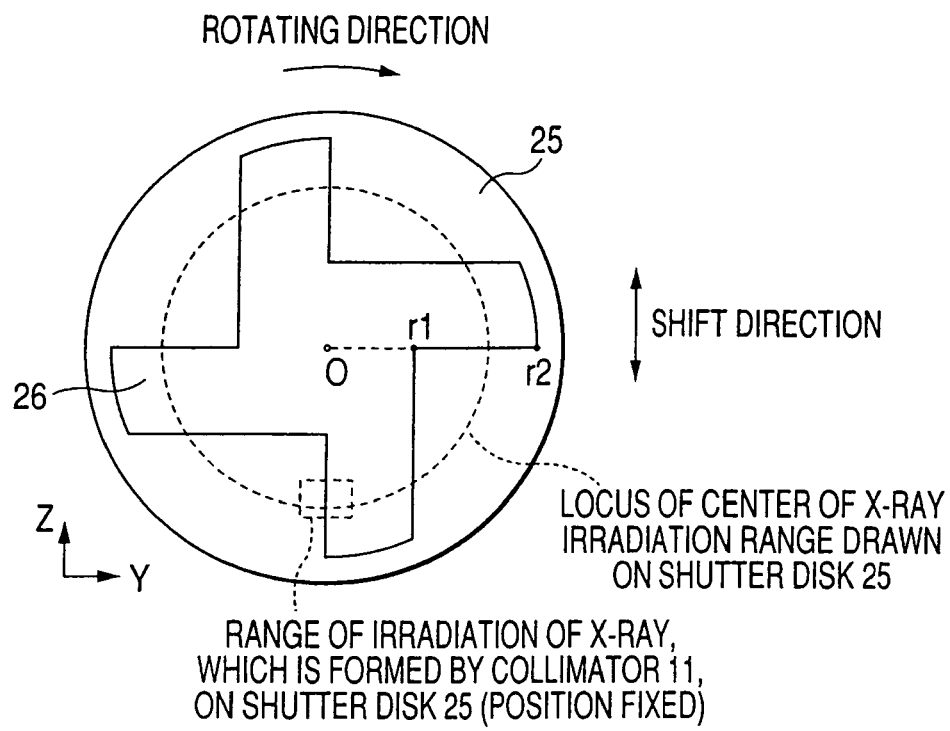
FIG. 4 is a diagram showing shift of the shutter disk in FIG. 2.

FIG. 4 shows another specific example of the shape of the aperture 26. In this example, four apertures 26 are formed at a constant interval (90°) in a circumferential direction as in the above-mentioned example. In this example, again, the number of apertures 26 is not required to be limited to four. Each of the apertures 26 has an aperture width with an aperture ratio 1.0 in a range from the center O of the disk 25 to the radius r1. In other words, the four apertures 26 are united in this range. Each of the apertures 26 has an aperture width with an aperture ratio continuously falling from 1.0 to 0.3 in the range from the radius r1 to the radius r2. With such a structure, the aperture ratio of the apertures 26 changes continuously and steplessly with respect to the radial direction of the disk 25. In other words, the apertures 26 are formed in the disk 25 having the shape shown in FIG. 4 such that the shutter effect increases steplessly from the center of the disk 25 toward the outer circumference thereof.

Figure 12:
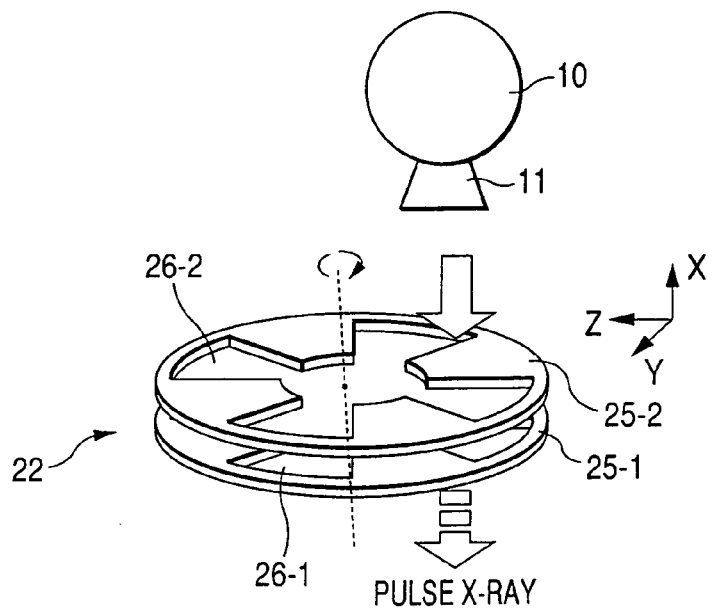
FIG. 12 is a plan view showing another structure of the shutter mechanism in FIG. 1.

FIG. 12 shows the shutter mechanism 22 of another structure. This shutter mechanism 22 has two shutter disks 25-1 and 25-2 that are stacked. Apertures 26-1 and 26-2 are formed in the shutter disks 25-1 and 25-2, respectively. The apertures 26-1 and 26-2 have a shape in which an aperture ratio in a circumferential direction of the shutter disks 25-1 and 25-2 is constant with respect to a radial direction thereof. An angular difference of one of the shutter disks 25-1 and 25-2 with respect to the other is variable. By changing this angular difference, an aperture ratio of an aperture, which is formed by combining the apertures 26-1 and 26-2, changes. The shutter mechanism 22 includes a mechanism for changing the angular difference of one of the shutter disks 25-1 and 25-2 with respect to the other. In addition, the shutter mechanism 22 includes a mechanism for rotating the shutter disk 25-1 and the shutter disk 25-2 in the same direction at the same speed while keeping the set angular difference between the shutter disk 25-1 and the shutter disk 25-2.

The shutter disk 25 of the shape shown in FIG. 3 or the shutter disk 25 of the shape shown in FIG. 4 is mounted on the shutter disk rotation mechanism. The shutter disk rotation mechanism may include a mechanism for attaching and detaching the shutter disk 25 such that the shutter disk 25 of the shape shown in FIG. 3 and the shutter disk 25 of the shape shown in FIG. 4 are mounted arbitrarily and selectively.

Figure 5:
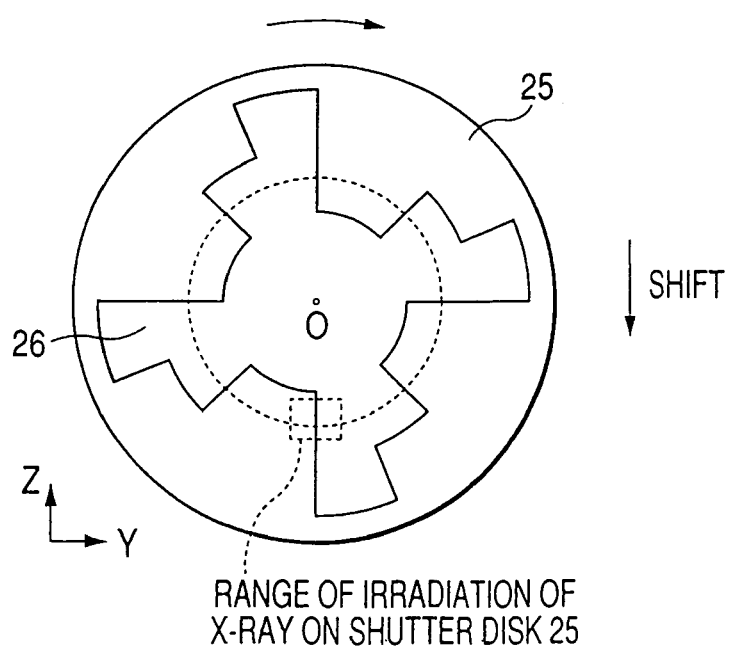
FIG. 5 is a plan view showing another structure of the shutter disk in FIG. 2.
Figure 6:
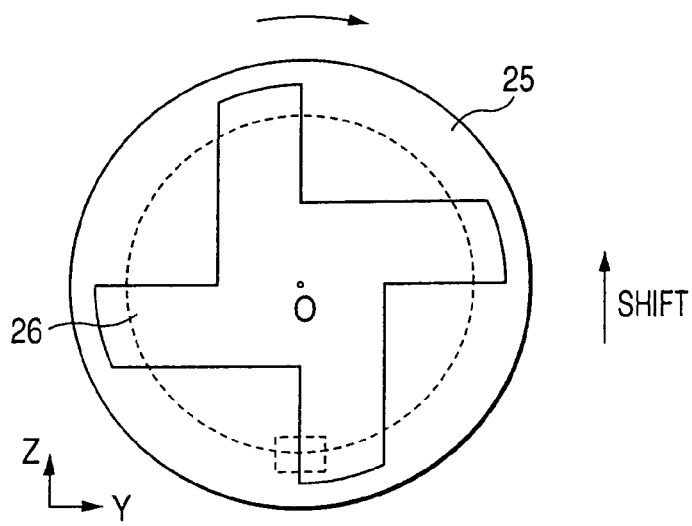
FIG. 6 is a diagram showing shift of the shutter disk in FIG. 5.

As indicated by arrows in FIGS. 3 and 4, a shutter shift mechanism 19 includes a structure, which supports the shutter disk 25 so as to be movable (shift freely) back and forth in a radial direction (parallel to an Z axis) together with the shutter disk rotation mechanism, and a drive system, which drives a shift of the shutter disk 25 and the shutter disk rotation mechanism. Since the X-ray tube 10 and the collimator 11 are fixed to the rotary frame 12, by shifting the shutter disk 25, a center position of an X-ray spot irradiated on the shutter disk 25 moves along the radial direction of the shutter disk 25 as shown in FIGS. 5 and 6. This movement makes it possible to switch irradiation of continuous X-rays on a subject and irradiation of a pulse X-ray on the subject while continuously generating X-rays by reducing a load on the high-voltage generator 21 and to change a pulse width of the pulse X-ray.

A cabinet 3 includes system controller 29 that controls an operation of the entire system, a scan controller 30, a pre-processing unit 34 for correcting X-ray signals (digital projection data) collected by the data collection apparatus 24, a data storage 35 for storing projection data and storing restructured image data, a restructuring unit 36 that restructures image data on the basis of the projection data, a display processor 37, a display 38, an input device 39 including a mouse and a keyboard, a shutter controller 41 for controlling the shift of the shutter disk 25 by the shutter shift mechanism 19, and a trigger generator 42 for generating a data collection trigger of the data collection apparatus 24. The trigger generator 42 counts a pulse, which is outputted from a rotary encoder 20 every time the shutter disk 25 rotates by a very small angle, and generates a trigger at timing when the number of counts has reached a reference value. The reference value is predefined as a number corresponding to an interval of the apertures 26 of the shutter disk 25, for example, 90°. Consequently, a data collection cycle can be synchronized with timing of irradiation of a pulse X-ray on a subject in accordance with the rotation of the shutter disk 25.

Next, operations of this embodiment will be explained. First, as a data collection operation, as described above, the data collection apparatus 24 repeats the data collection cycle for collecting X-ray signals from the X-ray detector 23 in accordance with triggers that are outputted from the trigger generator 42 repeatedly at a constant cycle. The data collection cycle includes a charge storage period, a charge read-out period, and a reset period. Charges generated in the charge storage period are stored in capacitors corresponding to respective detection elements, read out to the data collection apparatus 24 from the respective detection elements as a current signal in the charge read-out period, converted into a voltage signal, amplified, and further converted into digital data. The capacitors are reset in the reset period before the next data collection cycle. A period from a trigger to the next trigger is referred to as a view period in this context. A scan is defined as an operation for collecting projection data while the X-ray tube 10 rotates around a subject by 360° or (180°+fan angle) required for restructuring of one piece tomographic image data. The scan is executed repeatedly in continuous rotation.

Since the continuous X-rays are converted into the pulse X-ray according to the rotation of the shutter disk 25, fluctuation in a cycle of the pulse X-ray can be controlled to stabilize. Moreover, switching from the continuous X-rays to the pulse X-ray and speed-up of change of a pulse width are realized accurately according to the shift of the shutter disk 25. With such an advantage, this embodiment makes it possible to switch the continuous X-rays to the pulse X-ray and to change a pulse width for each scan and even during a scan period.

Figure 7:
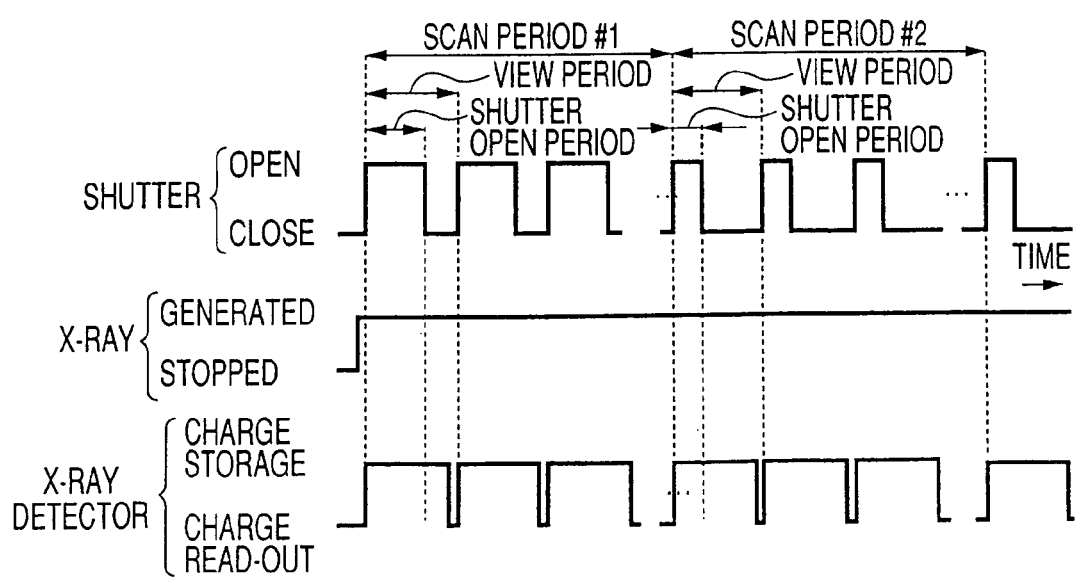
FIG. 7 is a diagram showing a change in a shutter open period for each scan by a shutter controller in FIG. 1.

FIG. 7 shows an operation for changing a pulse width of a pulse X-ray for each scan according to this embodiment in a form of a time chart. Note that, in the following explanation, it is assumed that the shutter disk 25 has the structure shown in FIG. 3. A rotation speed of the shutter disk 25 is adjusted in accordance with a time length of a view period from a trigger to the next trigger. In other words, a rotation speed of the shutter disk 25 is controlled by the scan controller 30 on the basis of an output pulse of the rotary encoder 20 such that the aperture 26 of the shutter disk 25 comes to an X-ray irradiation position on the shutter disk 25 at the same cycle as a trigger cycle, that is, when the number of apertures 26 formed in the shutter disk 25 is n, a time required for rotating the shutter disk 25 by an angle of 360°/n coincides with the trigger cycle (view period). In addition, the trigger generator 42 shifts a trigger pulse temporally on the basis of an output pulse of the rotary encoder 20 such that a trigger rises in synchronization with the beginning of a shutter open period according to the rotation of the shutter disk 25.

A tube voltage with a constant amplitude is continuously applied to the X-ray tube 10 from the high-voltage generator 21 over all scans. In addition, a filament heating current is supplied continuously at a constant amplitude such that a tube current with a constant amplitude flows continuously to the X-ray tube 10 over all the scans. Consequently, X-rays are continuously generated from the X-ray tube 10 at a constant radiation quality and a constant dose over all the scans.

In a certain scan period #1 during continuous scans, under the control of the shutter shift controller 41, a position of the shutter disk 25 is adjusted by the shutter shift mechanism 19 such that an irradiation position of an X-ray from the collimator 11 on the shutter disk 25 is within, for example, the range from the radius r1 to the radius r2 of the shutter disk 25. Consequently, a pulse X-ray having a pulse width equivalent to 70% of the view period is irradiated on a subject repeatedly at a cycle equivalent to the trigger cycle.

In the next scan period #2, a position of the shutter disk 25 is shifted by the shutter shift mechanism 19 such that an irradiation position of an X-ray from the collimator 11 on the shutter disk 25 is within the range from the radius r2 to the radius r3 of the shutter disk 25. Consequently, a pulse width changes, and a pulse X-ray having a pulse width equivalent to 30% of the view period is irradiated on the subject repeatedly at the cycle equivalent to the trigger cycle.

The change of a pulse width for each scan is effective in, for example, a scan of a system in which a scan position of a subject changes during continuous scans such as a multi-slice scan or a helical scan. It is not preferable from the viewpoint of a reduction in exposure to irradiate an X-ray on a portion with a low X-ray attenuation at a dose equivalent to that in a portion with a high X-ray attenuation. Such unnecessary exposure can be avoided by changing a pulse width for each scan according to movement of a scan portion.

An operator may change a pulse width of a pulse X-ray at arbitrary timing with a manual operation via the input device 39. Alternatively, it is also possible that preferable pulse widths are determined in advance with respect to plural scan positions, respectively, in the shutter shift controller 41 on the basis of scanogram data, which is acquired at the time of scan planning in advance, and a pulse width of a pulse X-ray is automatically changed according to the preferable pulse widths. Moreover, it is also possible that a pulse width is determined in the shutter shift controller 41 on the basis of projection data, which is collected in an immediately preceding scan or a scan earlier than that, during continuous scans, and a pulse width of a pulse X-ray is changed dynamically according to the determined pulse width. A method of changing a pulse width is arbitrary in this way.

Figure 8:
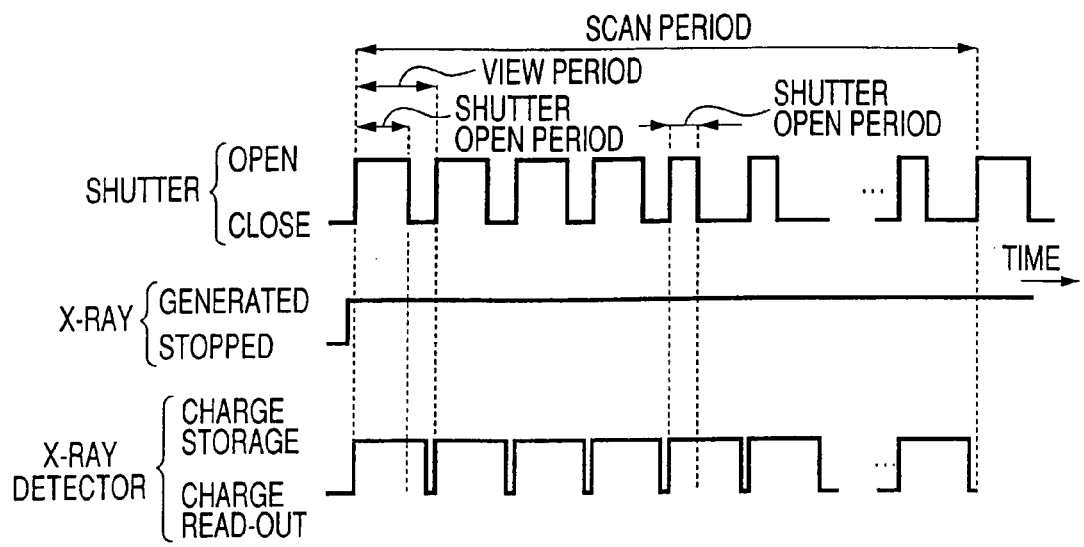
FIG. 8 is a diagram showing a change in a shutter open period during a period of scan by the shutter controller in FIG. 1.

FIG. 8 shows an operation for changing a pulse width of a pulse X-ray during a scan period according to this embodiment in a form of a time chart. At the beginning of the scan period, under the control of the shutter shift controller 41, a position of the shutter disk 25 is adjusted by the shutter shift mechanism 19 such that an irradiation position of an X-ray from the collimator 11 on the shutter disk 25 is, for example, within the range from the radius r1 to the radius r2 of the shutter disk 25. Consequently, a pulse X-ray having a pulse width equivalent to 70% of the view period is irradiated on a subject repeatedly at a cycle equivalent to the trigger cycle.

At a certain point during the same scan period, a position of the shutter disk 25 is shifted by the shutter shift mechanism 19 such that an irradiation position of an X-ray from the collimator 11 on the shutter disk 25 is within the range from the radius r2 to the radius r3 of the shutter disk 25. Consequently, a pulse width changes, and a pulse X-ray having a pulse width equivalent to 30% of the view period is irradiated on a subject repeatedly at a cycle equivalent to the trigger cycle.

As in the example of FIG. 7, an operator may change a pulse width of a pulse X-ray at arbitrary timing with a manual operation via the input device 39. Alternatively, it is also possible that preferable pulse widths are determined in advance with respect to plural scan positions, respectively, in the shutter shift controller 41 on the basis of scanogram data, which is acquired from multiple directions at the time of scan planning in advance, and a pulse width of a pulse X-ray is automatically changed according to the preferable pulse widths. Moreover, it is also possible that a pulse width is determined in the shutter shift controller 41 on the basis of projection data, which is collected at a point a half rotation earlier, one rotation earlier, or several rotations earlier, during continuous scans, and a pulse width of a pulse X-ray is changed dynamically according to the determined pulse width. A method of changing a pulse width is arbitrary in this way.

A change of a pulse width during a scan period can show an exposure reduction effect in all scans such as a single slice scan, a multi-slice scan, and a helical scan. In particular, in the multi-slice scan and the helical scan, the effect is further improved by using the system of FIG. 8 together with the system of FIG. 7.

Figure 9:
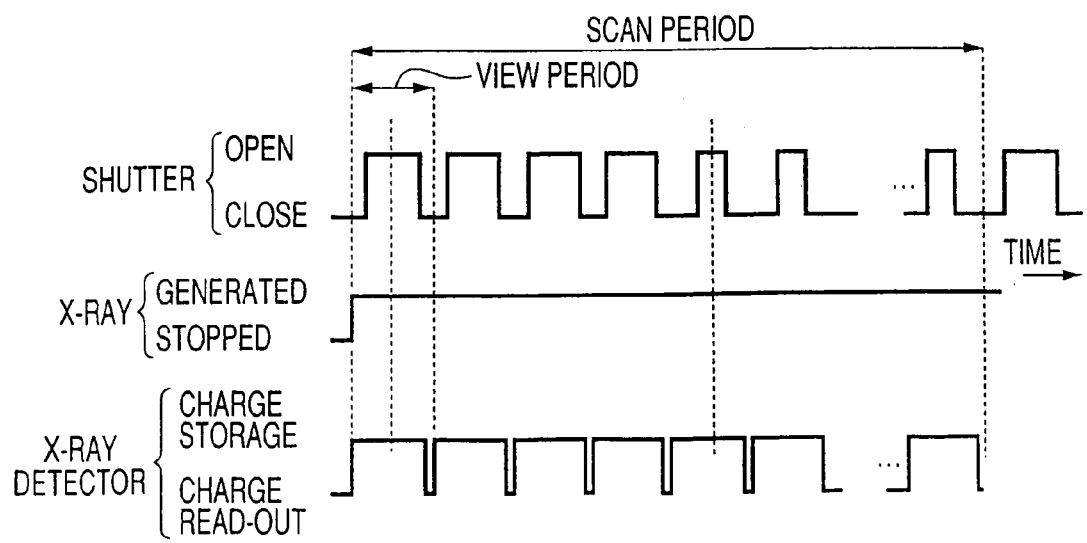
FIG. 9 is a diagram showing a trigger shift function by a trigger generator in FIG. 1 in comparison with FIG. 7.
Figure 10:
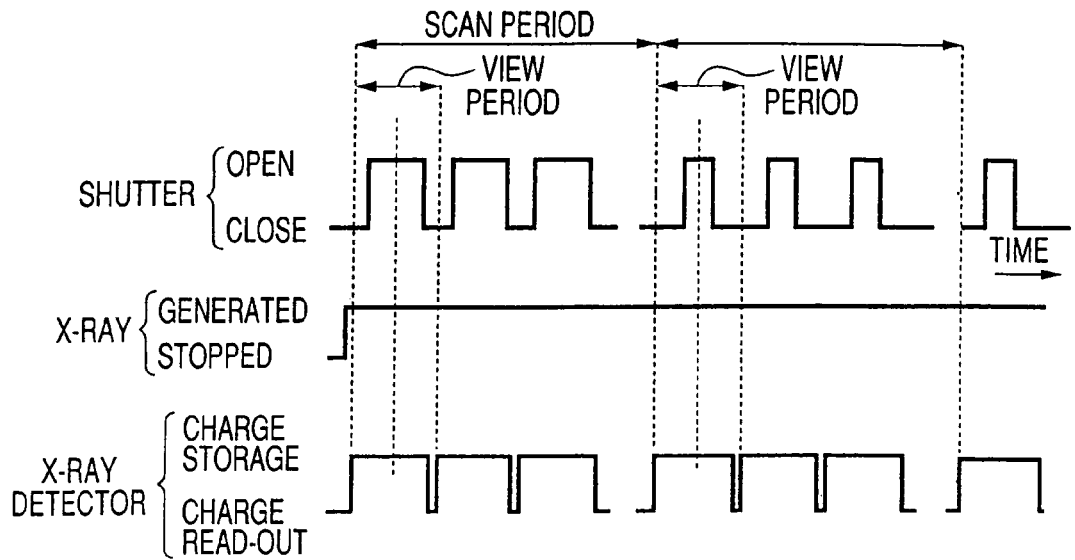
FIG. 10 is a diagram showing the trigger shift function by the trigger generator in FIG. 1 in comparison with FIG. 8.

In the above explanation, the trigger generator 42 shifts a trigger pulse temporally on the basis of an output pulse of the rotary encoder 20 such that a trigger rises in synchronization with the beginning of a shutter open period according to the rotation of the shutter disk 25. However, as shown in FIGS. 9 and 10, a temporal shift amount of a trigger pulse may be changed according to a position of the shutter disk 25 such that a center of the view period or the charge storage period coincides with a center of the shutter open period according to the rotation of the shutter disk 25 or such that the view period begins after a delay time corresponding to the shutter open period elapsed from the beginning of the shutter open period. Consequently, a situation, in which a period of X-ray irradiation on a subject partially deviates from the charge storage period, due to unsteadiness of rotation of the shutter disk 25 can be prevented effectively.

Figure 11A:
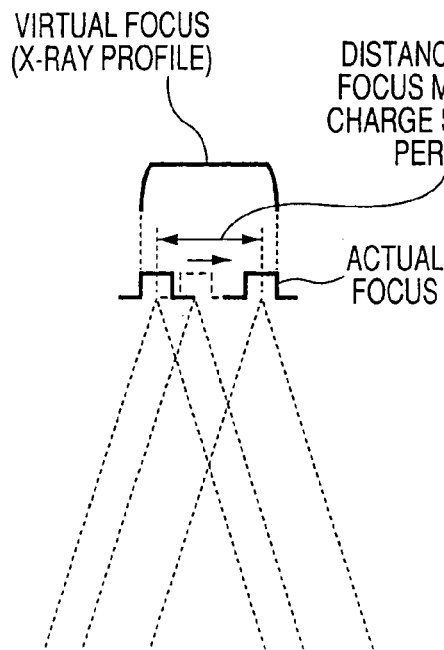
FIGS. 11A and 11B are diagrams showing a size-down effect for a virtual focus that is realized together with a reduction in exposure according to this embodiment.
Figure 11B:
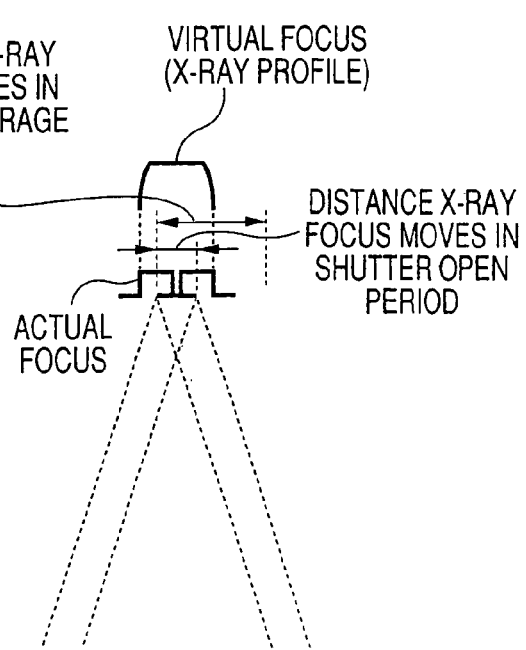

As described above, according to this embodiment, unnecessary exposure can be avoided by converting continuous X-rays into a pulse X-ray with a shutter mechanism. In addition, since a pulse width can be changed, the exposure reduction effect can be facilitated as required. Further, effects as described below can also be realized. As described above, projection data reflects an amount of charges that is generated following incidence of an X-ray during the charge storage period. Since the X-ray tube 10 continues rotating even during the charge storage period, as shown in FIG. 11A, an X-ray focus expands virtually along a rotating direction of the X-ray tube 10. As it is well known, when the X-ray focus expands, a spatial resolution deteriorates. Conventionally, for a reduction in exposure, a dose of continuous X-rays is reduced by tube current control to cope with the deterioration of the spatial resolution. Therefore, the deterioration of the spatial resolution still remains. In this embodiment, the exposure reduction effect can be realized together with improvement of the spatial resolution. In this embodiment, a reduction in exposure according to necessity is realized by pulse width control under a constant dose. Therefore, as shown in FIG. 11B, even during the same charge storage period as that in the conventional technique, an irradiation period for an X-ray can be reduced. In accordance with the reduction in the irradiation period for an X-ray, virtual expansion of an X-ray focus is controlled, and the deterioration of the spatial resolution can be controlled.

Figure 13:
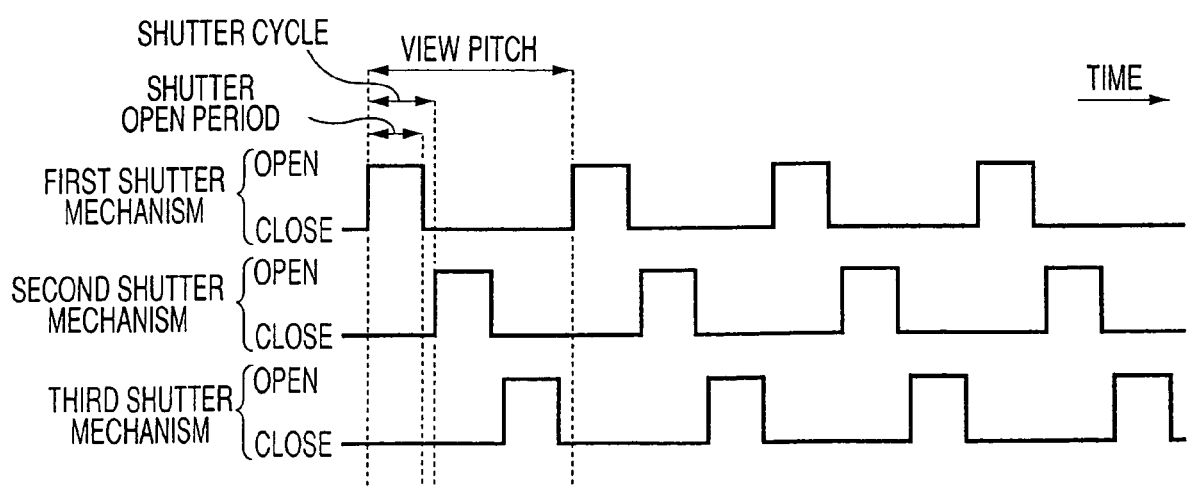
FIG. 13 is a diagram showing control of a shutter controller in FIG. 1 with respect to plural shutter mechanisms that are mounted on a multi-tube type X-ray CT.

This embodiment is also applicable to a so-called multi-tube type in which plural pairs of an X-ray tube and an X-ray detector are mounted on a rotary frame. For example, in the case in which three X-ray tubes and three X-ray detectors are mounted on a rotary frame, respectively, three shutter mechanisms 22 are mounted for three X-ray tubes, respectively. In order to avoid a situation in which scattered radiations affect each other, the scan controller 30 controls rotation phases of the disks 25 of the three shutter mechanisms 22 such that open periods of the three shutter mechanisms 22 do not overlap each other (see FIG. 13). Initially, the open periods are set to be shorter than alternating cycles of the three shutter mechanisms 22. Consequently, even if the open periods deviate from each other more or less, it can be guaranteed that the open periods of the three shutter mechanisms 22 do not overlap each other.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computer tomography apparatus, comprising:
an X-ray tube that generates an X-ray;
an X-ray detector for detecting an X-ray transmitted through a subject;
a collection unit that collects X-ray signals from the X-ray detector repeatedly;
a shutter mechanism unit that is arranged between the X-ray tube and the subject in order to convert the generated X-ray into a pulse X-ray and is constituted such that a ratio of a shutter open period and a shutter close period is variable;
a restructuring unit that restructures image data on the basis of the collected X-ray signals: and
a control unit that controls the shutter mechanism unit in order to change the ratio of a shutter open period and a shutter close period;
wherein the control unit changes the ratio of a shutter open period and a shutter close period dynamically during a helical scan; and
wherein the control unit calculates the ratio of a shutter open period and a shutter close period individually with respect to plural slice positions on the basis of scanogram data of the subject.

2. An X-ray computer tomography apparatus according to claim 1, wherein the control unit controls the shutter mechanism unit in accordance with the calculated ratio.

3. An X-ray computer tomography apparatus according to claim 1, wherein the shutter mechanism has a disc-like X-ray shielding plate having at least one aperture that is arranged substantially perpendicular to a center axis of the X-ray and is formed such that an aperture ratio in a circumferential direction thereof changes with respect to a radial direction thereof.

4. An X-ray computer tomography apparatus according to claim 3, wherein the aperture unit is formed such that the aperture ratio changes stepwise with respect to the radial direction.

5. An X-ray computer tomography apparatus according to claim 3, wherein the aperture is formed such that the aperture ratio changes continuously with respect to the radial direction.

6. An X-ray computer tomography apparatus according to claim 1, wherein the shutter mechanism includes: plural disc-like X-ray shielding plates with a variable angle difference that are stacked and have at least one aperture; and a rotation mechanism that rotates the plural X-ray shielding plates.

7. An X-ray computer tomography apparatus, comprising:
an X-ray tube that generates an X-ray;
an X-ray detector for detecting an X-ray transmitted through a subject;
a collection unit that collects X-ray signals from the X-ray detector repeatedly;
a shutter mechanism unit that is arranged between the X-ray tube and the subject in order to convert the generated X-ray into a pulse X-ray and is constituted such that a ratio of a shutter open period and a shutter close period is variable;
a restructuring unit that restructures image data on the basis of the collected X-ray signals;
a control unit that controls the shutter mechanism unit in order to change the ratio of a shutter open period and a shutter close period;
wherein the shutter mechanism has a disc-like X-ray shielding plate having at least one aperture that is arranged substantially perpendicular to a center axis of the X-ray and is formed such that an aperture ratio in a circumferential direction thereof changes with respect to a radial direction thereof; and
wherein the shutter mechanism includes: a rotation mechanism that axially rotates the X-ray shielding plate; and a movement mechanism that moves the X-ray shielding plate in the radial direction of the X-ray shielding plate together with the rotating mechanism.

8. An X-ray computer tomography apparatus according to claim 7, wherein the control unit control the movement mechanism in order to move the X-ray shielding plate in the radial direction to change the ratio.

9. An X-ray computer tomography apparatus according to claim 7, further comprising an input unit that inputs a physical constitution of the subject, wherein the control unit moves the X-ray shielding plate on the basis of the inputted physical constitution of the subject.

10. An X-ray computer tomography apparatus according to claim 7, wherein the control unit controls the movement mechanism on the basis of scanogram data of the subject.

11. An X-ray computer tomography apparatus according to claim 7, wherein the control unit moves the X-ray shielding plate on the basis of an X-ray signal at a point a half rotation earlier or an angle rotation integer times the half rotation earlier.

12. An X-ray computer tomography apparatus according to claim 7, further comprising: a detection unit for detecting rotation of the X-ray shielding plate; and a trigger generation unit that generates a trigger for promoting the collection of the X-ray signals on the basis of an output of the detection unit.

13. An X-ray computer tomography apparatus according to claim 12, wherein the trigger generation unit generates a trigger such that a pulse width of the X-ray is at least within the cycle.

* * * * *